United States Patent [19]

Sjoquist et al.

[11] Patent Number: 5,285,792
[45] Date of Patent: Feb. 15, 1994

[54] SYSTEM FOR PRODUCING PRIORITIZED ALARM MESSAGES IN A MEDICAL INSTRUMENT

[75] Inventors: Steven E. Sjoquist, Lynnwood; John C. Daynes, Redmond, both of Wash.

[73] Assignee: Physio-Control Corporation, Redmond

[21] Appl. No.: 819,200

[22] Filed: Jan. 10, 1992

[51] Int. Cl.$^5$ .............................................. A61B 5/04
[52] U.S. Cl. ...................................... 128/697; 607/27; 607/29
[58] Field of Search ............ 128/419 PT, 419 D, 697; 324/73.1; 340/519; 607/5, 27, 29

[56] References Cited

U.S. PATENT DOCUMENTS

| | | | |
|---|---|---|---|
| 3,798,596 | 3/1974 | Sumiyoshi et al. | 340/519 X |
| 3,988,730 | 10/1976 | Valker | 340/519 X |
| 4,216,462 | 8/1980 | McGrath et al. | 340/150 |
| 4,227,526 | 10/1980 | Goss | 128/DIG. 13 |
| 4,383,241 | 5/1983 | Kojima et al. | 340/519 X |
| 4,488,555 | 12/1984 | Imran | 128/419 PT |
| 4,532,934 | 8/1985 | Kelen | 128/697 |
| 4,749,985 | 6/1988 | Corsberg | 340/519 X |
| 4,763,066 | 8/1988 | Yeung et al. | 324/73.1 |
| 5,172,698 | 12/1992 | Stanko | 128/697 |

Primary Examiner—Lee S. Cohen
Assistant Examiner—Jeffrey R. Jastrzab
Attorney, Agent, or Firm—Christensen, O'Connor, Johnson & Kindness

[57] ABSTRACT

A defibrillator/monitor (10) employing a message processing routine (60) that controls the way in which information from a plurality of sensing circuits (28) is communicated to an attending physician by output devices (30). In that regard, each of the various conditions monitored by the sensing circuits has a priority associated therewith. Each condition may be associated with one or more of five different types of messages: an initial display message, steady state display message, initial sound message, steady state sound message, and display icon message. The different messages, like the different conditions, may also be prioritized. The particular message or messages produced by the output devices in response to a particular set of conditions is then dependent upon the relative prioritization of the conditions and messages as evaluated by a microcomputer (18) in accordance with the routine.

16 Claims, 6 Drawing Sheets

SYSTEM FOR PRODUCING PRIORITIZED ALARM MESSAGES IN A MEDICAL INSTRUMENT

FIELD OF THE INVENTION

This invention relates generally to medical instruments and, more particularly, to messages generated by such instruments.

BACKGROUND OF THE INVENTION

A variety of instruments have been developed for use in the monitoring and treatment of medical conditions. Many such instruments provide a physician with information regarding a patient's condition, as well as information concerning the nature and effectiveness of any treatment provided. Often, the accuracy and availability of this information is dependent upon the operability of the instrument itself.

As might be expected, however, it may be difficult for the physician to continuously monitor all of the information available from the instrument, let alone evaluate the operability of the instrument. This problem is compounded when a number of instruments are being used simultaneously in the treatment of the patient. The problem may become particularly acute in an emergency situation, when the physician's attention is primarily focused upon the patient.

To ensure that important information is promptly called to the physician's attention, conventional medical instruments often produce messages associated with various patient, treatment, or instrument events. These messages may be in a variety of different forms. For example, in addition to a visible display, an audible message or alarm will often be employed to communicate the desired information in the event the instrument is outside the physician's field of view.

One type of medical instrument that conventionally provides a user with some form of messages is the defibrillator/monitor. A monitor portion of the instrument typically monitors the electrical activity of the patient's heart via two or more electrodes attached to the patient. A defibrillator portion of the instrument is used to, for example, apply a relatively large pulse of electrical energy to the patient via a pair of electrodes, to terminate fibrillation of the heart. The instrument may also include a pacing section that applies smaller periodic pulses of current to the patient's heart to cause the heart to beat at some desired rate.

Reviewing the message capabilities of certain prior art defibrillator/monitors, a number of different defibrillator/monitors are manufactured by Physio-Control, assignee of the present application. One such instrument is the LIFEPAK 8 defibrillator/monitor. The LIFEPAK 8 instrument is constructed to provide the attending physician with a variety of different messages.

Some of these messages are produced to apprise the physician of the patient's condition. For example, information from the monitor portion of the instrument is used to generate messages indicating that the patient's heart rate has crossed preset thresholds. Other messages provide the physician with information regarding the treatment being administered to the patient. For example, the defibrillator portion of the instrument initiates messages identifying the amount of energy discharged to the patient by the defibrillator. Still other messages contain information about the operability of the instrument. For example, information from sensing circuits included in the instrument is used to generate messages reflecting the condition of the instrument's batteries and the general service condition of the device.

The messages produced by the LIFEPAK 8 defibrillator/monitor include some visible and some audible messages. The visible messages may be as simple as lit indication lights. Each of the different visible messages is generally produced by a separate display element or separate segment of a display. With such dedicated displays used, however, the complexity of the instrument's face panel increases with the number of different messages to be produced.

The audible messages produced by the LIFEPAK 8 defibrillator/monitor are simple tones. Although audible messages may be especially suitable for conveying information to a physician in an emergency setting, the use of audible messages is relatively limited in the LIFEPAK 8 product.

Another prior art defibrillator/monitor of interest is the LIFEPAK 200 instrument manufactured by Physio-Control. The LIFEPAK 200 defibrillator/monitor includes a liquid crystal display (LCD), which generates a variety of different visible messages. In that regard, operator messages prompt an operator regarding the proper use and operation of the instrument. The LCD also allows six different instrument condition messages to be displayed.

The instrument condition messages include a "service" message, indicating that a self-diagnostic program run by the instrument has detected some fault in instrument readiness. A "low battery" message indicates that battery voltage, as monitored by a simple comparator, has dropped below some preset threshold. A "no tape" message indicates that a sensor included in the instrument's cassette recorder has not detected the presence of a cassette tape. A "tape" message further indicates that another sensor has determined that a cassette loaded into the recorder is either jammed or at the end of the tape.

Several messages produced by the LIFEPAK 200 are a function of the impedance of the interface formed between the patient and a pair of electrodes coupled to the instrument, as measured by an impedance measurement circuit. In that regard, a "connect electrodes" message indicates that the impedance has exceeded a preset threshold, suggesting that the electrodes are not adequately attached to the patient. Similarly, a "motion detected" message indicates that variations in the impedance of the patient/electrode interface have been detected, reflecting some patient/electrode disturbance.

Along with the various visible messages described above, the LIFEPAK 200 instrument also produces coded audible tones to prompt the operator and alert the operator to the presence of the warning messages described above. Each of the visible and audible messages is produced as soon as the associated instrument condition is detected. The messages have fixed durations and are immediately replaced by any messages associated with subsequently detected conditions.

As will be appreciated, although the message scheme used by the LIFEPAK 200 generally works well, it may have certain limitations when a number of message conditions occur simultaneously or over a short interval of time. Because the scheme treats all messages the same, a message associated with a relatively important condition may be replaced almost immediately with a message of lesser importance, depending upon the time at which the various conditions are detected. Similarly, while the LIFEPAK 200 message scheme provides the user with a message when the associated condition is first detected, it does not remind the user of the continued presence of the condition.

In view of the preceding observations, it would be desirable to produce a medical instrument that is able to provide an operator with a wide variety of messages without requiring an unduly complex display arrangement. It would also be desirable to ensure that relatively important messages are recognized as such and called to the operator's attention promptly and in several different formats. Finally, it would be desirable to ensure that some indication of an ongoing condition can be provided to the operator, particularly when the condition is of relative importance.

SUMMARY OF THE INVENTION

In accordance with this invention, a medical instrument is provided including a sensing element, message element, and prioritization element. The sensing element monitors the operation of the instrument to detect a plurality of predetermined conditions. The message element generates a message indicative of the predetermined conditions. The prioritization element controls the generation of messages by the message element in accordance with a predetermined set of parameters.

In accordance with a further aspect of this invention, a method is provided for controlling the reaction of a medical instrument to a plurality of different conditions identified by the instrument. The method includes the step of establishing a different priority for each of the different conditions. At least one of a plurality of outputs is then associated with each different condition. An output associated with a particular condition identified by the instrument is then produced, the particular output produced being dependent upon the duration of time since the particular condition was identified, whether any other conditions have been identified, and the priorities of the particular condition and any other conditions identified.

In accordance with yet another aspect of this invention, a method is provided for controlling the production of a plurality of messages by a medical instrument. The messages are produced in response to a plurality of different conditions identified by the instrument and at least some of the plurality of different messages are produced by the same portion of the medical instrument. The method involves the establishment of a different priority for each of the different conditions and a different priority for each of the plurality of different messages produced by the same portion of the instrument. A message associated with a particular condition is then produced at the same portion of the instrument, the particular message produced being dependent upon the priority of the particular condition and the priorities of the different messages produced by the same portion.

In accordance with additional aspects of this invention, a medical instrument may include an initial message generation element for producing an initial message, in response to the sensing of a predetermined condition by a sensing element, for a predetermined interval of time. A steady state message generation element then produces a steady state message upon the expiration of the predetermined interval of time. Alternatively, the instrument may include a textual message generation element for producing a textual message, an icon message generation element for producing an icon, and an audible message generation element for producing an audible message, each such message being produced in response to the sensing of a predetermined condition by some sensing element.

BRIEF DESCRIPTION OF THE DRAWINGS

The invention will presently be described in greater detail, by way of example, with reference to the accompanying drawings, wherein.

DETAILED DESCRIPTION OF THE PREFERRED EMBODIMENT

Figure 1:
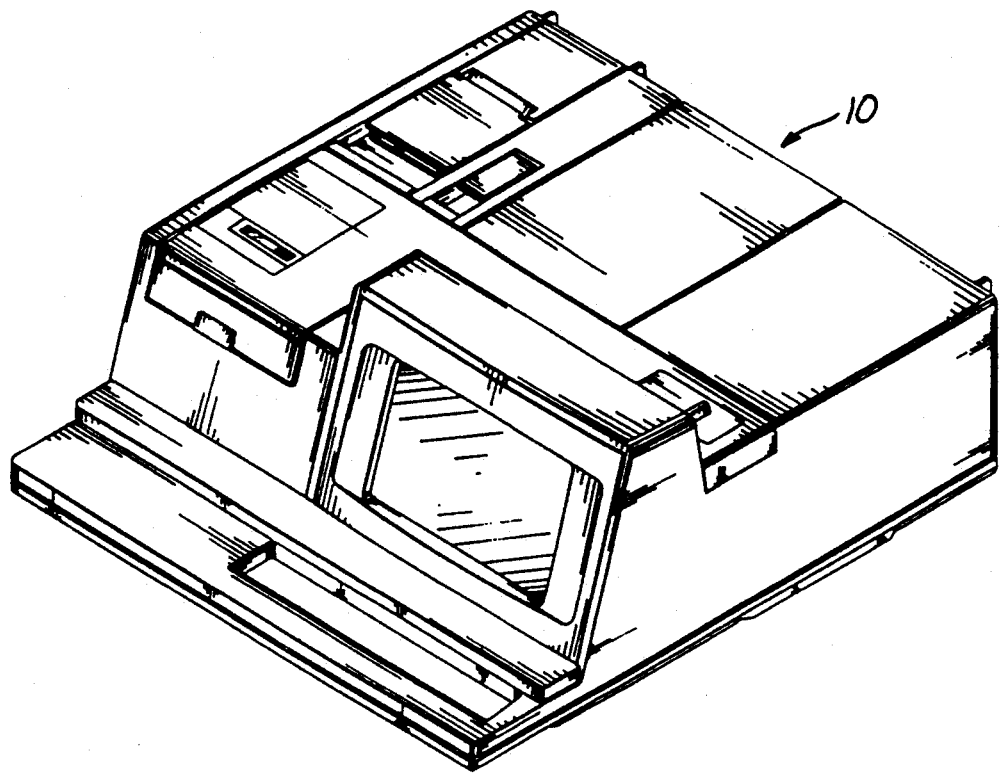
FIG. 1 is an illustration of a medical instrument suitable for employing a message processing scheme designed in accordance with the present invention.

Referring now to FIG. 1, a medical instrument constructed in accordance with the present invention is shown. In the arrangement illustrated, the instrument is a defibrillator/monitor 10. The defibrillator/monitor 10 is electrically coupled to a patient by one or more sets of electrodes (not shown).

As will be described in greater detail below, the defibrillator/monitor 10 receives electrocardiographic (ECG) signals from the patient's heart for use in analysis and display. The defibrillator/monitor 10 is also constructed to apply relatively large pulses of energy to the patient to terminate fibrillation of the patient's heart. In addition, the defibrillator/monitor 10 may be constructed to allow lower current pacing pulses to be periodically applied to the patient's heart to induce a desired heart rate.

In accordance with the present invention, the defibrillator/monitor 10 provides the user with a plurality of prioritized messages in response to a variety of different conditions monitored by the instrument. These conditions may relate to, for example, the operability of the instrument, the health of the patient, the treatment administered to the patient, and the performance of the attending operator. The messages produced by the defibrillator/monitor 10 may include various types of visible and audible messages, whose prioritized production allows a relatively large number of different conditions to be called to the user's attention, while ensuring that the most recent and important information is readily available to the user.

Figure 2:
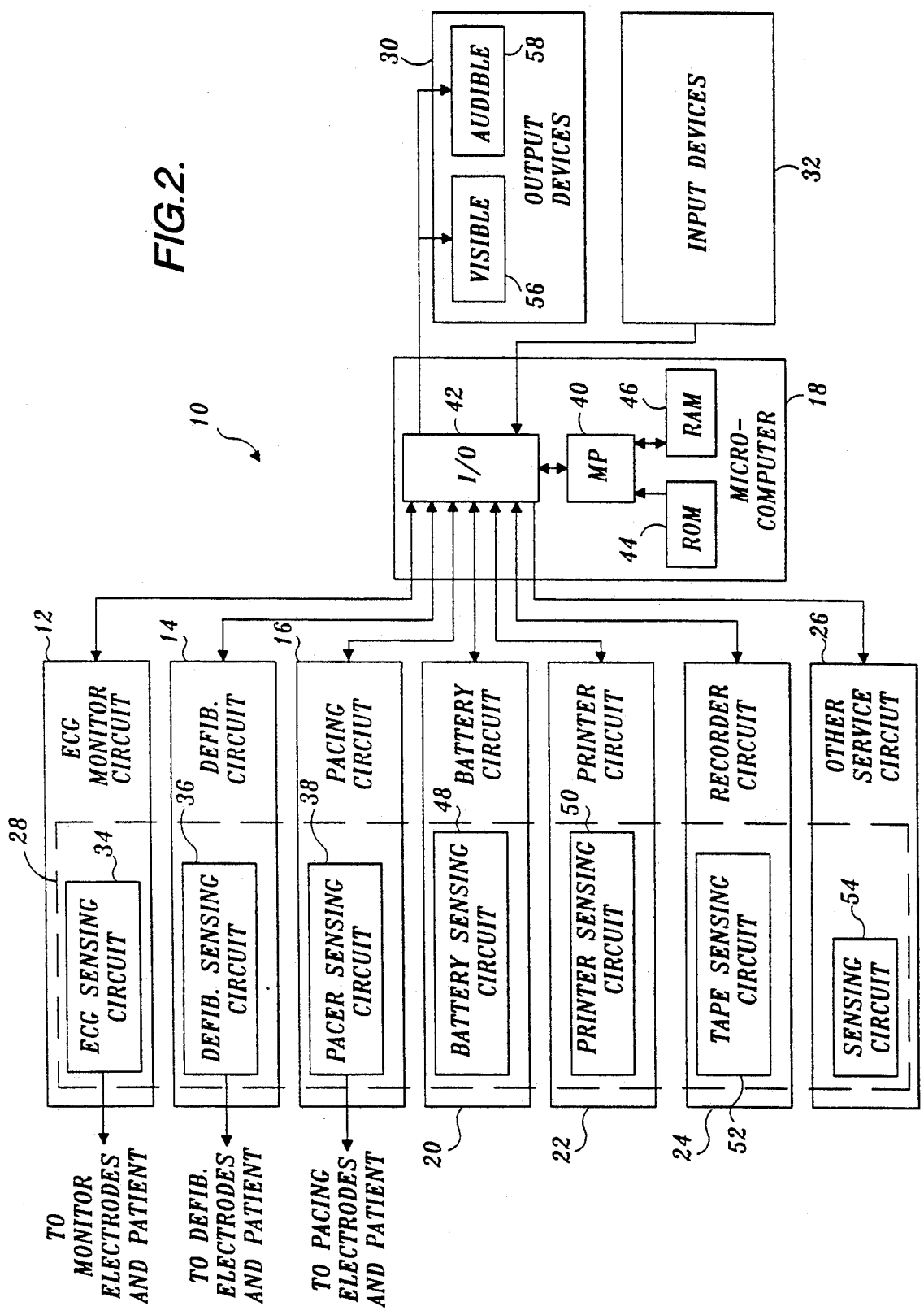
FIG. 2 is a block diagram illustrating various components that may be included in an instrument of the type shown in FIG. 1.

Before providing a more detailed discussion of the way in which the various messages are processed, the basic components of the defibrillator/monitor 10 will be considered in conjunction with the block diagram of FIG. 2. In that regard, the defibrillator/monitor 10 includes an ECG monitor circuit 12, defibrillator circuit 14, and pacing circuit 16 under the common control of a microcomputer 18. Instrument 10 also includes a battery circuit 20, printer circuit 22, recorder circuit 24, and other services circuit 26. The various circuits noted above include sensing circuits that are collectively represented in FIG. 2 by block 28.

The defibrillator/monitor 10 also includes output devices 30 coupled to the microcomputer 18. As will be described in greater detail below, the output devices 30 produce the various messages under the control of microcomputer 18. Finally, input devices 32 are included to allow the operator to input information to, and initiate control of, the defibrillator/monitor 10.

Reviewing each of these various components of defibrillator/monitor 10 in somewhat greater detail, the ECG monitor circuit 12 is of conventional design. In that regard, monitor circuit 12 is preferably constructed for use with two or more limb electrodes to monitor three leads of ECG information, conventionally designated I, II, and III. Monitor circuit 12 may also be constructed for use with an additional six precordial electrodes to monitor an additional nine leads of ECG information, designated aVR, aVL, aVF, and V1-V6.

Because the monitor circuit 12 is of conventional design, a detailed discussion of its construction is unnecessary. Functionally, however, the monitor circuit 12 filters the signals received from the patient via the various electrodes to remove undesired components attributable to, for example, noise. The signals are also amplified to levels suitable for further processing and may be subjected to some form of calibration to ensure that they are within a suitable range.

As would be expected, the monitor circuit 12 is also responsible for sampling the signals received from the various electrodes and processing them in conventional fashion to provide the desired leads of information. The monitor circuit 12 further typically includes some form of isolation circuitry to prevent current from being applied to the patient via the monitoring electrodes in the event of an instrument fault and to protect the monitoring circuit 12 from transients introduced by the defibrillation circuit 14 or pacing circuit 16.

The final component of the monitor circuit 12 to be discussed is the ECG sensing circuit 34. This circuit may be constructed to monitor any of a plurality of different parameters of the ECG information collected from the patient by the monitor circuit 12, as well as other aspects of the monitor circuit's operation. Outputs representative of the sensed parameters are then provided to microcomputer 18 for use, for example, by the message processing software.

By way of illustration, the sensing circuit 34 may include a conventional circuit, such as an R-wave counter, that is designed to monitor the repetition frequency of the ECG signal. As will be appreciated, this circuit monitors the ECG signal for the recurrence of some easily identified periodic feature. In addition, the ECG sensing circuit 34 may be constructed to identify features of the ECG signal for use by, for example, the defibrillator circuit 14 in a synchronized cardioversion mode of operation. The sensing circuit 34 may also be designed to produce an output representative of the particular ECG lead or leads being monitored by circuit 12, as well as an output representative of whether or not an analysis of the received patient signal indicates that the patient is moving.

Like monitor circuit 12, the defibrillator circuit 14 is of conventional construction. Briefly reviewing the construction of defibrillator circuit 14, the defibrillator circuit 14 is typically coupled to the patient via a pair of defibrillation electrodes or paddles. One or more capacitors are employed to store energy for discharge to the patient via the electrodes. The amount of energy stored on the capacitor is selected by the operator from any one of a plurality of discrete energy levels typically ranging up to 360 joules. The defibrillator circuit 14 may also be constructed to ensure that the stored energy represents a calibrated value.

Typically, the defibrillator circuit 14 includes a discharge control circuit that is responsible for controlling the discharge of the stored energy to the patient. In that regard, energy is discharged to the patient, via a pair of electrodes applied to the patient's chest, when the attending physician presses one or more discharge switches located on the instrument or electrodes. In a synchronized mode of operation, once the switches have been actuated, the control circuit determine the precise time at which a discharge should occur relative to the cardiac cycle monitored by monitor circuit 12. Further, the control circuit determines the rate at which the energy is discharged, i.e., the shape of the discharge pulse, once discharge has been initiated.

The defibrillator circuit 14 also includes a defibrillation sensing circuit 36. As will be appreciated, sensing circuit 36 is constructed to monitor various aspects of the defibrillation circuit's operation. For example, sensing circuit 36 may be designed to monitor the energy stored on by the capacitor for discharge to the patient as well as the timing of any such discharges. Further, the sensing circuit 36 may provide outputs to microcomputer 18 indicating whether a discharge was performed in the manual or synchronized mode of operation.

Turning now to a discussion of the pacing circuit 16, this circuit is also of conventional design. The pacing circuit 16 is typically coupled to the patient via a pair of pacing electrodes applied to the patient's chest. The pacing circuit 16 applies relatively low level, periodic current pulses to the electrodes and patient's heart to induce the desired patient heart rate.

In that regard, the pacing circuit 16 includes a pacing control circuit that allows an operator to select the magnitude of the pacing current from any one of a plurality of different levels. Similarly, the operator is able to set the desired pacing rate at any one of a plurality of different levels extending from, for example, 40 to 90 beats per minute. The shape of the repetitive pulses is also determined by the control circuit.

The control circuit included in pacing circuit 16, also typically allows the circuit 16 to be operated in either a demand or nondemand mode of operation. In the nondemand mode, the application of pacing pulses to the patient is initiated and terminated by the operator. In the demand mode of operation, the control circuit monitors the ECG information obtained by monitor circuit 12 to determine when pacing is required. Like monitor circuit 12, pacing circuit 16 also includes isolation circuitry to protect the patient in the event of an instrument fault and to protect the pacing circuit 16 from transients introduced by the defibrillation circuit 14.

The pacing circuit 16 further includes a pacer sensing circuit 38. This circuit 38 monitors various aspects of the operation of the pacing circuit 16. For example, sensing circuit 38 may be designed to produce outputs indicative of the magnitude and repetition rate of the pacing current delivered to the patient. Similarly, an output may be provided to microcomputer 18 to indicate whether the pacing is being performed in the demand or nondemand mode of operation.

Reviewing now the construction of microcomputer 18, microcomputer 18 receives inputs from the various sensing circuits 28 and input devices 32. These inputs are processed to provide the desired control of the various components of defibrillator/monitor 10. Of particular interest in the present context, the microcomputer 18 also processes these various inputs to provide an operator with a prioritized scheme of messages at output devices 30, alerting the operator to a plurality of different conditions of interest.

As shown in FIG. 2, the microcomputer 18 includes a microprocessor 40. An input/output circuit 42 processes the various inputs and outputs to microcomputer 18 to provide the desired interface between microprocessor 40 and the other components of defibrillator/monitor 10. A read-only memory (ROM) 44 is programmed with instructions used by microprocessor 40 in the control of the defibrillator/monitor 10. As will be described in greater detail below, these instructions include a message processing routine used by microprocessor 40 in providing the prioritized generation of messages at output devices 30. A random access memory (RAM) 46 is used by the microprocessor 40 to store information processed during execution of the various programs stored in ROM 44.

Reviewing now the battery circuit 20, circuit 20 allows the defibrillator/monitor 10 to be used, for example, in field applications in which an alternative power supply is not readily available. The battery circuit 20 includes one or more batteries whose various specifications, including voltage and current ratings, charge life, recharge rate, chemical construction, and size, are dependent upon desired performance characteristics. As will be appreciated, the battery circuit 20 may include some form of adaptor for coupling the instrument directly to an alternative source of power, either to operate the instrument or to recharge the batteries. Because the design of such batteries is well known, further details are not provided herein.

As indicated in FIG. 2, battery circuit 20 also includes a battery sensing circuit 48. The sensing circuit 48 may be, for example, a voltmeter used to monitor the voltage across the batteries' terminals. In that case, the output of the battery sensing circuit 48, provided to microcomputer 18, is proportional to battery voltage. Alternatively, sensing circuit 48 may be some form of comparator, which compares the battery voltage against one or more preset thresholds determined by microcomputer 18. In that event, the output of sensing circuit 48 may simply indicate whether the battery voltage has crossed the particular threshold or thresholds. Sensing circuit 48 may also be constructed to produce outputs indicating when, for example, auxiliary power is being used to power the instrument or recharge the batteries.

The printer circuit 22 is also of conventional design and provides a printed record of various types of information obtained from the monitor circuit 12, defibrillator circuit 14, and pacing circuit 16. The printer circuit 22 commonly employs a thermal printhead to record information on an adjacent spool of thermally sensitive paper. As will be appreciated, the printer circuit 22 also includes various components required to drive the paper past the print head.

A printer sensing circuit 50 is included in circuit 22 to monitor one or more parameters of the printer's operation. For example, an optoelectronic sensor, having an optical path interrupted by paper loaded into the printer, may be employed to detect the presence or absence of paper. Another sensor responsive to the operation of one or more of the paper drive components may be used to sense the operation of the printer circuit 22. As will be appreciated, the various outputs of sensing circuit are applied to microcomputer 18.

Like printer circuit 22, the tape recorder circuit 24 is of conventional design. The tape recorder circuit 24 is included to provide a second record of various types of information received from the monitor circuit 12, defibrillator circuit 14, and pacing circuit 16. Given the comparatively large storage capacity of the conventional audiocassette tapes used with recorder circuit 24, the tape record is typically more extensive than the printed record. As will be appreciated, the tape recorder circuit 24 includes the various drive, recording, and control elements required for storing and retrieving information from the cassette tapes used.

As shown in FIG. 2, the tape recorder circuit 24 also includes a tape sensing circuit 52, constructed to provide microcomputer 18 with outputs representative of a variety of different aspects of the recorder circuit's operation. For example, an optoelectronic device having a light path interrupted by a tape inserted into the recorder circuit 24 can be used to detect the presence or absence of an audio cassette in the recorder. Further, sensing elements associated with the tape drive circuitry may be employed to monitor, for example, the operation of recorder circuit 24 or an end of tape condition.

As will be appreciated, other service circuits 26 may be included in the defibrillator/monitor 10 as desired. For example, the defibrillator/monitor 10 might include a circuit for linking the instrument to other instruments such as auxiliary computers or storage devices. As shown in FIG. 2, each such service circuit 26 preferably includes a sensing circuit 54 used to produce outputs representative of one or more aspects of the service circuit's operation. By way of example, the sensing circuits 54 may monitor things like internal power supply voltages and the integrity of various memory and processor components associated with the different circuits.

Turning now to a brief review of the various output devices 30 included in defibrillator/monitor 10, as will be appreciated, any of a variety of devices can be employed. As shown in FIG. 2, at least one visible message device 56 and one audible message device 58 are preferably employed.

Figure 3:
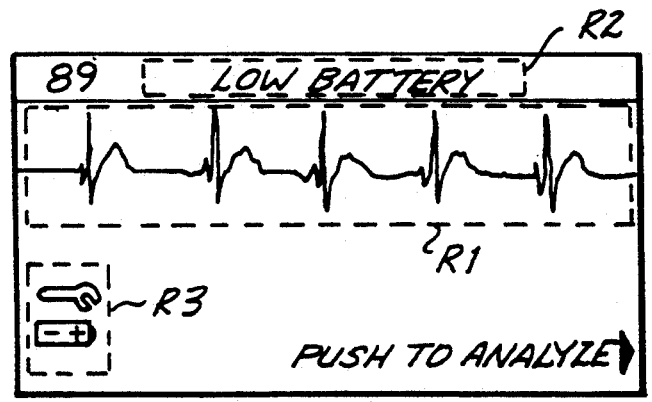
FIG. 3 is an illustration of a screen, included in the instrument of FIG. 1, to provide a variety of different visible messages in accordance with the present invention.

In that regard, the visible message device 56 is depicted in FIG. 3 as, for example, a conventional cathode ray tube (CRT) or liquid crystal display (LCD). The display is further divided into a plurality of display regions R. For example, the display includes a first region R1 used to display a trace of one of the leads of ECG information collected by monitor circuit 12. A second region R2 is used to display a plurality of different textual messages in accordance with the prioritization scheme implemented by microcomputer 18. A third region R3 of the display is used to display a select number of icons associated with the messages of region R2, also in accordance with the prioritized scheme.

The audible output device 58 may include, for example, a tone oscillator, a voice synthesizer, and a speaker or horn. The tone oscillator responds to inputs from microcomputer 18 by providing outputs, having distinct frequencies and patterns, to the speaker. As a result, the speaker is able to generate various sequences of sounds. Similarly, the voice synthesizer provides the speaker with inputs used to provide verbal messages.

In the preferred arrangement, the outputs of the tone oscillator and voice synthesizer cause the speaker to produce at least a short alarm, delayed continuous alarm, and low battery sound. The short alarm is a sequence of three 100 millisecond tones, each of which has a frequency of 1046 Hertz. The tones are separated by silent intervals of 150 milliseconds and a 200 millisecond pause is included at the end of each short alarm sequence. The delayed continuous alarm is simply a repeated sequence of a 20 second silence, followed by one short alarm.

The low battery sound is a sequence of two 100 millisecond tones, each of which has a frequency of 1000 Hertz. The tones are separated by a 100 millisecond gap. At the end of this sequence, there is a 200 millisecond pause, followed by the words "low battery," produced by the speaker in response to an output from the voice synthesizer.

Finally, the input devices 32 typically include a plurality of push buttons and selector switches included on the defibrillator/monitor 10. The input devices 32 are used by the operator to input information regarding the desired operating characteristics of defibrillator/monitor 10. For example, input devices 32 allow the operator to select particular ECG leads to be received by monitor circuit 12, select the energy level to be discharged by the defibrillator circuit 14 as well as the time as which a discharge occurs, and select the magnitude and repetition rate of the current pulses delivered by pacing circuit 16.

Figure 4:
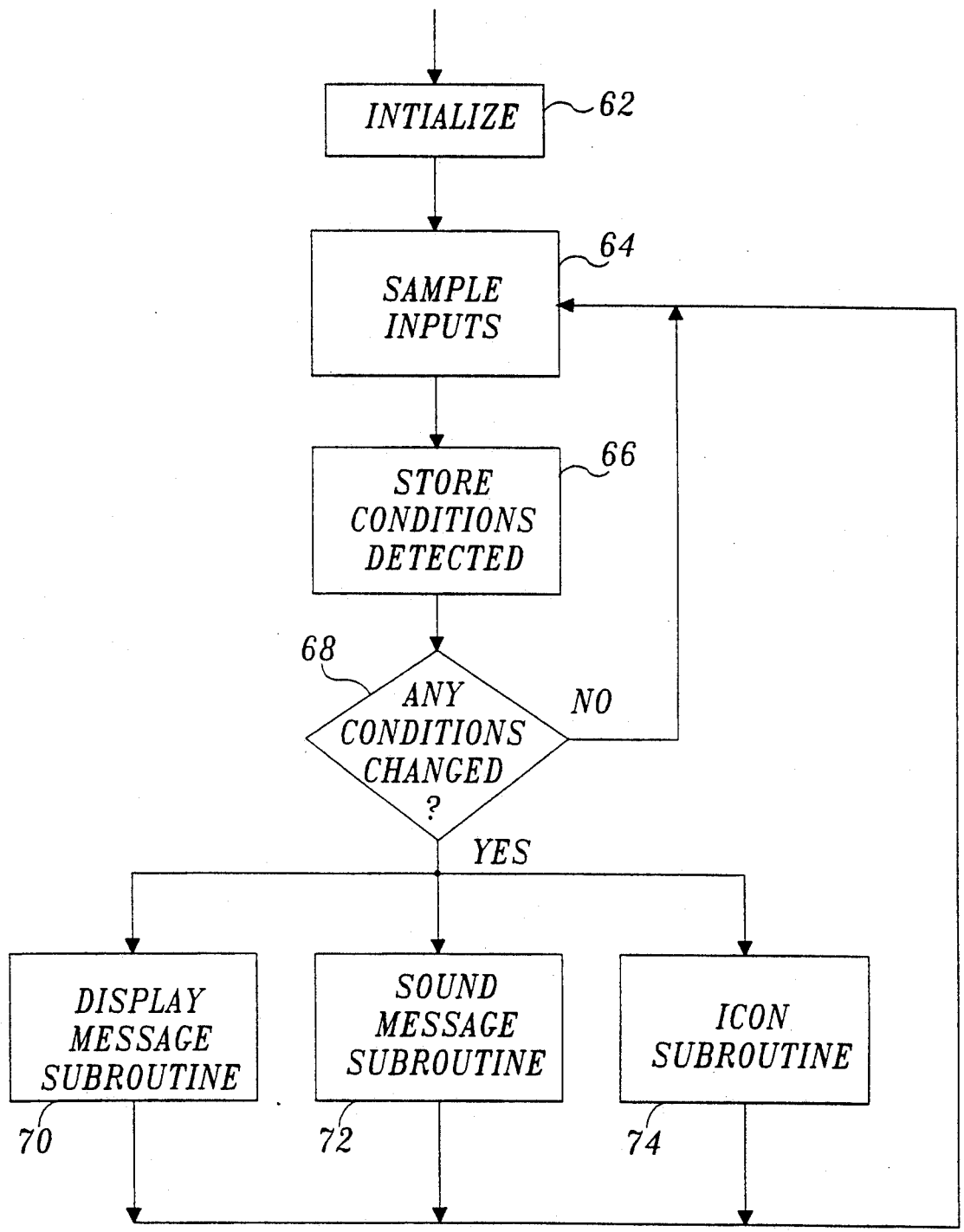
FIG. 4 is a flow chart illustrating the initial portion of a message processing routine used by the instrument of FIG. 1 to generate a plurality of different messages.

Having reviewed the construction of the various components of defibrillator/monitor 10, a message processing routine 60 stored in ROM 44 for use by microprocessor 42 in controlling the generation of messages at output devices 30 will be considered. A flow chart depicting the operation of the message processing routine 60 is shown in FIG. 4. Before discussing routine 60 in detail, however, a little background information will be provided regarding the scheme implemented by the routine.

In that regard, the routine 60 is designed to control the production of messages relating to a variety of patient, instrument, treatment, and/or operator conditions detected by sensing circuits 28. Each of these conditions is assigned a priority and has at least one of five different types of messages associated therewith. The different types of messages produced by the same output device, or same part of an output device, are also prioritized relative to each other. Routine 60 then controls the production of messages based upon the times at which the various conditions are detected, the identities and priorities of the conditions detected, and the relative priorities of the messages to be produced in association with the conditions.

As noted above, in the currently preferred arrangement, one or more of five different types of messages is associated with each condition of interest monitored by sensing circuits 28. These messages include a new display message, a steady state display message, a new sound message, a steady state sound message, and a display icon message.

Reviewing each of these types of messages individually, the initial display message is a textual message produced in region R2 of the visible display 56. The initial display message includes, for example, one or two lines of text that vary depending upon the particular condition the message is associated with. The message is activated for roughly two seconds after the associated condition is detected and the lines of text are alternately flashed at one second intervals.

The steady state display message is also a one or two line textual message produced in region R2 of the visible display 56. The steady state display message is typically activated after the initial display message is extinguished, provided that the associated condition is still detected by sensing circuits 28. The lines of text of the steady state display message are alternatively flashed at one second intervals until the associated condition is no longer detected by the sensing circuits 28, or until a higher priority message is produced in region R2 of display 56 as described in greater detail below.

The initial sound message and steady state sound message are similar to the initial display message and steady state display message in several respects. In that regard, the initial sound message is produced by the audible output device 58 concurrently with the initial display message discussed above. The steady state sound message is, likewise, produced by device 58 concurrently with the steady state display message.

Finally, the display icons associated with particular conditions detected by sensing circuits 28 are generally produced in region R3 of visible display 56 when the associated conditions are detected. The icons then remain displayed until the associated conditions are no longer detected or until replaced by higher priority icons, as described in greater detail below.

As previously noted, any of the five types of messages produced by the same portion of an output device are prioritized relative to each other. Thus, in the arrangement described above, the initial and steady state display messages produced in region R2 of display 56 are prioritized relative to each other. Similarly, the initial and steady state sound messages produced by audible device 58 are prioritized relative to each other.

In both cases, such messages are identified as either high priority messages, intermediate priority messages, or low priority messages. The initial display and sound messages are classified as high priority messages and always interrupt intermediate or low priority messages produced in region R2 of display 56 or by audible device 58, should they be present. The intermediate priority messages are associated with specialized operator prompts, discussed in greater detail below.

Steady state display and sound messages are low priority messages. As a result, high priority and intermediate priority messages can interrupt a steady state display message in region R2 of display 56 or a steady state sound message produced by device 58 at any time. If more than one condition has been detected by sensing circuits 28, only the steady state message associated with the condition having the highest priority is displayed.

Because the icons are generated by region R3 of display 56, they can be produced simultaneously with the initial and steady state messages and do not require prioritization relative to those messages. Instead, the particular icons displayed depend upon the relative priorities of the associated conditions detected. In the currently preferred arrangement, the two highest priority conditions having different icons associated therewith are identified and the region R3 then displays only those two icons.

Before turning to a discussion of the message processing routine 60 in conjunction with FIG. 4, it will be recalled that the various conditions monitored by the sensing circuits 28 are prioritized in accordance with a second priority scheme, independent of that used to prioritize the types of messages. Under this scheme, the conditions of interest are ranked in order of their importance to the attending physician. The highest priority is then assigned to the most important condition, with progressively lower priorities assigned to those conditions of lesser importance.

Turning now to FIG. 4, the message processing routine 60 begins with an initialization step 62 at which, for example, the desired priorities are assigned to the different conditions to be detected by sensing circuits 28. Then, at block 64 the outputs of sensing circuits 28 are monitored to determine which of the various conditions of interest have been detected. The identity of these conditions is stored at block 66 and a test performed at block 68 to determine whether there has been any change in the conditions detected.

In that regard, the conditions stored at block 66 may reflect the detection of some new condition, not previously present, by sensing circuits 28. Alternatively, a previously detected condition may no longer be present. As yet another alternative, the conditions stored at block 66 may reflect both the present of one or more newly detected conditions and the absence of one or more previously detected conditions.

If block 68 determines that there has been no change in the conditions detected, routine 60 restores operation to block 64, without revising any of the messages previously displayed by output devices 30. On the other hand, if some change in conditions has been detected, the routine proceeds along three parallel subroutines 70, 72, and 74.

Figure 5:
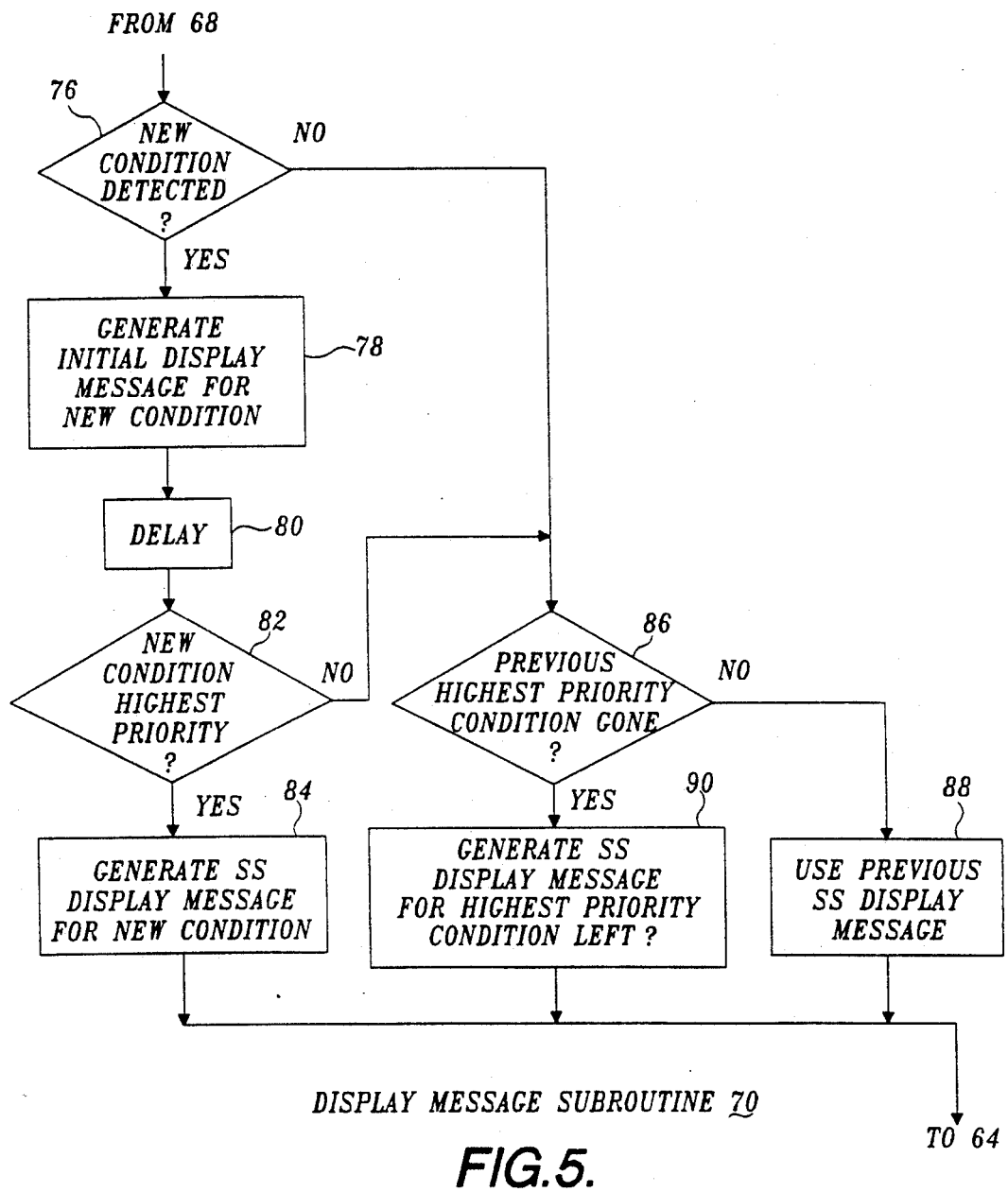
FIG. 5 is a flow chart elaborating upon a display message subroutine included in the message processing routine of FIG. 4.

Reviewing these subroutines individually, the display message subroutine 70 is shown in greater detail in FIG. 5. Subroutine 70 begins at block 76 by performing a test to determine whether the change in conditions detected at block 68 is attributable, at least in part, to the detection of a "new" condition, not previously present. If a new condition has been detected, block 78 causes the initial display message associated with the newly detected condition to be generated at region R2 of display 56. A roughly two second delay is then introduced at block 80 to ensure that the initial display message is not prematurely interrupted. Although not shown in FIG. 5, if there is no initial display message associated with the newly detected condition, blocks 78 and 80 of routine 70 would be bypassed.

Once the delay associated with the initial display message has expired, or in the event that a new condition was not detected, subroutine 70 addresses the production of the appropriate steady state display message. In that regard, assuming first that a new condition was detected and the delay associated with the initial display message has expired, a test is performed at block 82 to determine whether the priority of the new condition is higher than the priority of any other conditions presently detected and whether the new condition has a steady state display associated therewith. If both of these criteria are met, block 84 initiates the production of the steady state display message associated with the new condition at region R2 of display 56.

In the event that block 76 has not detected a new condition, or block 82 determines that the priority of a newly detected condition is not greater than that of the other detected conditions, the subroutine 70 proceeds to test block 86. Block 86 compares the conditions presently detected at block 64 with the conditions previously detected at block 64. If the highest priority condition having a steady state message associated therewith has remained unchanged, the previous steady state display message will again be generated at block 88. On the other hand, if the previous high priority condition is no longer present, block 90 generates the steady state message associated with the remaining condition having both the highest priority and a steady state display message. Of course, if no conditions have been detected, no steady state display message will be produced.

Figure 6:
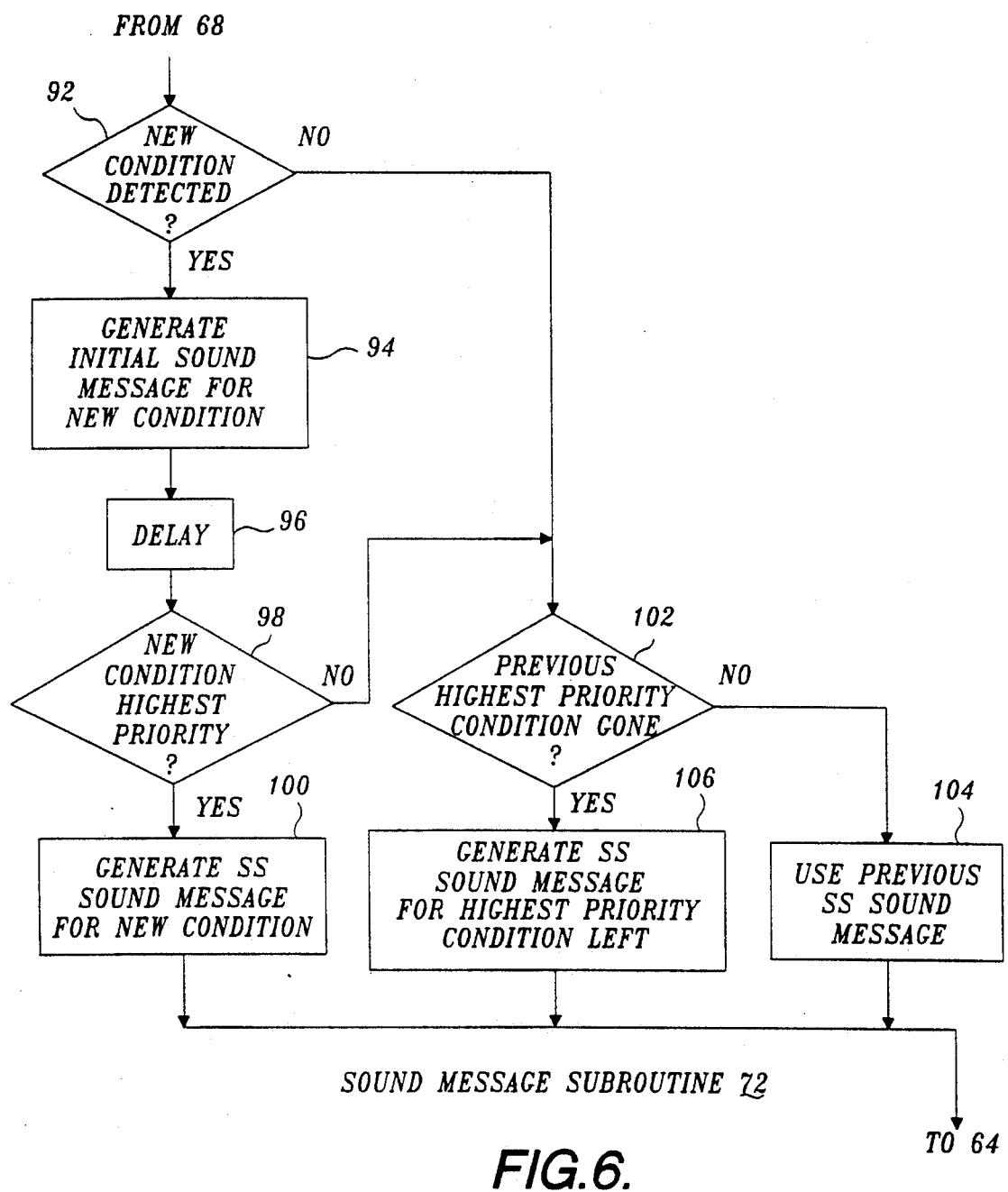
FIG. 6 is a flow chart elaborating upon a sound message subroutine included in the message processing routine of FIG. 4.

The sound message routine 72 is shown in greater detail in FIG. 6. Subroutine 72 begins at block 92 by performing a test to determine whether the change in conditions detected at block 68 is attributable, at least in part, to the detection of a new condition, not previously present. If a new condition has been detected, block 94 causes the initial sound message associated with the newly detected condition to be generated by audible device 58. A roughly two second delay is then introduced at block 96 to ensure that the initial sound message is not prematurely interrupted. Although not shown in FIG. 6, if there is no initial sound message associated with the newly detected condition, blocks 94 and 96 of subroutine 72 would be bypassed.

Once the delay associated with the initial sound message has expired, or in the event that a new condition was not detected, subroutine 72 addresses the production of the appropriate steady state sound message. In that regard, assuming first that a new condition was detected and the delay associated with the initial sound message has expired, a test is performed at block 98 to determine whether the priority of the new condition is higher than the priority of any other conditions presently detected and whether the new condition has a steady state display message associated therewith. If both of these criteria are met, block 100 initiates the production of the steady state sound message (if any) associated with the new condition at output device 58.

In the event that block 92 has not detected a new condition, or block 98 determines that the priority of a newly detected condition is not greater than that of the other detected conditions, the subroutine 72 proceeds to a test block 102. Block 102 compares the conditions presently detected at block 64 with the conditions previously detected at block 64. If the highest priority condition having a steady state display message associated therewith has remained unchanged, the previous steady state sound message will again be generated at block 104. On the other hand, if the previous high priority condition is no longer present, block 106 generates the steady state sound message associated with the remaining condition having both the highest priority and a steady state display message. Of course, if no conditions have been detected, no steady state sound message will be produced.

As will be appreciated from the preceding discussion, if each of the various conditions to be detected has an initial and steady state display message and an initial and steady state sound message associated therewith, the prioritization of the conditions used in message generation can be based solely upon the initialized ranking of the detected conditions. When some of the conditions do not have certain types of messages associated therewith, however, it may be desirable to consider not only the initialized ranking of the detected conditions, but whether or not they have certain types of messages associated therewith. In that regard, if the particular type of message being generated is not associated with certain conditions detected, it may be preferable to exclude them from the prioritization used to generate the message. In the arrangement described above, the generation of both display and sound messages is based upon the prioritization of detected conditions having display messages associated therewith. As will be appreciated, however, the generation of initial sound messages could be separately based upon the prioritization of detected conditions having sound messages associated therewith.

Figure 7:
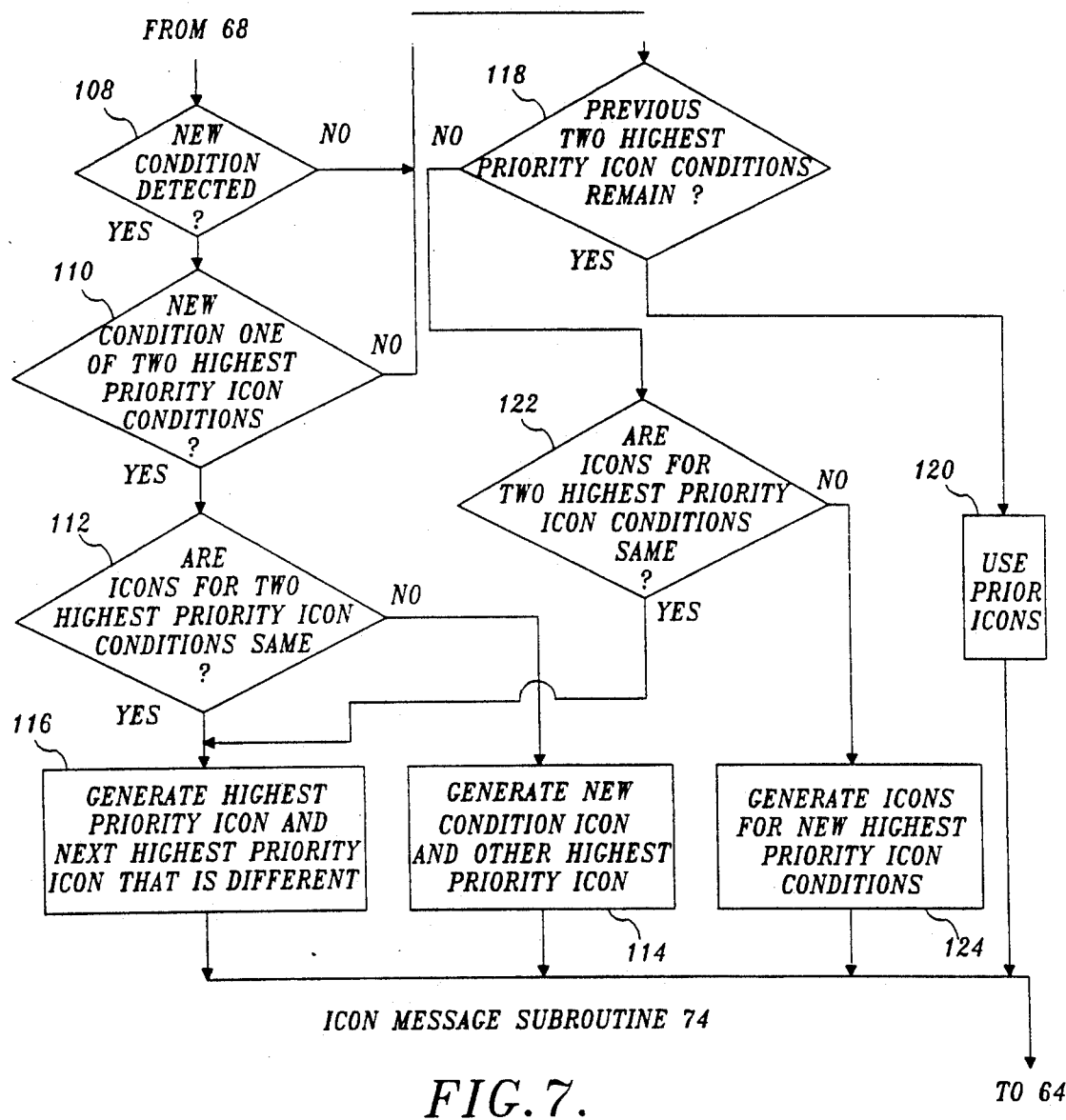
FIG. 7 is a flow chart elaborating upon an icon message subroutine included in the message processing routine of FIG. 4.

The icon message subroutine 74 is shown in greater detail in FIG. 7. As shown, subroutine 74 begins at block 108 by performing a test to determine whether the change in conditions detected at block 68 is attributable, at least in part, to the detection of a new condition, not previously present. In the event that a new condition has been detected, another test is performed at block 110 to determine whether the new condition is one of the two highest priority conditions stored at block 66. As will be appreciated, in the event that no icon display message is to be produced in conjunction with some of the conditions, block 110 determines whether the new condition is one of the two highest priority conditions that do have icons associated therewith.

If block 110 determines that the new condition is one of the two highest priority conditions associated with icons, yet another test is performed at block 112. There the subroutine 74 determines whether the same icon display message is associated both conditions. If the icon display messages associated with the two highest priority conditions are different, the icon display message for the new condition is then displayed by region R3 of device 56 at block 114, along with the icon display message associated with the other one of the two highest priority conditions. On the other hand, if the icon display messages for the two highest priority conditions are the same, the subroutine 74 will cause a single icon display message representative of both conditions to be produced at block 116, along with the icon display message associated with the next highest priority condition that is presently detected and that has an icon associated with it.

Assuming now that a new condition was not detected at block 108, or that a new condition was detected but was not one of the two highest priority icon conditions, as tested at block 110, the subroutine 74 proceeds to block 118. There, a test is performed to determine whether the two highest priority conditions having icons associated therewith are the same as the last time the inputs were sampled. If the two highest priority conditions have not changed, block 120 causes the previously displayed icon messages to be produced again by region R3 of output device 56.

On the other hand, if the two highest priority conditions are no longer the same, a new pair of icon display messages may be generated. In that event, the test discussed above in conjunction with block 112 is performed at block 122 to ensure that the same icon display message is not produced twice. If the icon display messages associated with the two highest priority conditions are different, those messages are generated by region R3 at block 124. Alternatively, block 116 will produce the icon display messages associated with the highest priority condition and the next highest condition having a different icon associated therewith. Of course, if only one condition having an icon associated therewith is detected, only one icon will be displayed and, if no such conditions are detected, no icons will be produced.

Once the three messages routines 70, 72, and 74 are completed, the flow of the message processing routine 60 is restored to block 64 where the sensing circuits are again polled. The entire process is then repeated continuously until the instrument is shut off.

In the currently preferred arrangement, the message processing routine 60 is used to process messages associated with eight different conditions primarily related to instrument readiness. These conditions, along with their associated priorities and messages are as follows:

1. Silence Alarm. priority=1; initial display message=none; steady state display message=none; initial sound message=none; steady state sound message=none; display icon=crossed bell; description=produced in response to an input from input devices 32 and initiated by the operator to disable another alarm produced by the instrument.

2. Service Defibrillator Alarm. priority=2; initial display message=SERVICE FAULT/CANNOT CHARGE; steady state display message=SERVICE FAULT/CANNOT CHARGE; initial sound message=short alarm; steady state sound message=none; display icon=wrench; description=produced in response to outputs from defibrillator sensing circuit 36 that disable the operation of the defibrillator circuit 14.

3. Service Alarm. priority=3; initial display message=SERVICE FAULT; steady state display message=SERVICE FAULT; initial sound message=short alarm; steady state sound message=none; display icon=wrench; description=produced in response to all service faults detected by various sensing circuits 28 that do not disable operation of defibrillator circuit 14.

4. Very Low Battery Alarm. priority=4; initial display message=REPLACE BATTERY; steady state display message=REPLACE BATTERY; initial sound message=short alarm; steady state sound message=delayed continuous alarm; display icon=battery; description=produced when the battery sensing circuit 48 determines that the battery voltage has fallen to a level that is inadequate to allow the defibrillator circuit 14 to charge or deliver the desired energy.

5. Low Battery Voltage. priority=5; initial display message=LOW BATTERY; steady state display message=LOW BATTERY; initial sound message=low battery sound; steady state sound message=delayed continuous alarm; display icon=battery; description=produced when the battery sensing circuit 48 determines that the battery voltage has fallen to a point that will allow power to be supplied to the instrument for only a relatively short time.

6. Printer Alarm. priority=6; initial display message=CHECK PRINTER; steady state display message=none; initial sound message=short alarm; steady state sound message=none; display icon=none; description=produced when the printer sensing circuit 50 determines that the printer needs to be checked by the operator due, for example, to an end of paper condition.

7. Tape Door Open Alarm. priority=7; initial display message=CLOSE TAPE DOOR; steady state display message=CLOSE TAPE DOOR; initial sound message=short alarm; steady state sound message=delayed continuous alarm; display icon=cassette tape; description=produced when the tape sensing circuit 52 determines that the tape door is open.

8. Tape Fault Alarm. priority=8; initial display message=CHECK TAPE; steady state display message=none; initial sound message=short alarm; steady state sound message=none; display icon=cassette tape; description=produced when the tape sensing circuit 52 determines that no cassette tape is present or the end of the tape has been reached.

Illustrating the way in which the message processing routine 60 would respond to the occurrence of different ones of these conditions, suppose that the sensing circuit 36 of defibrillator circuit 14 first detects a service defibrillator alarm condition. An initial display message of SERVICE FAULT/CANNOT CHARGE is generated at region R2 of display 56. A short alarm initial sound sequence is also generated. At the end of the initial display message and sound sequence, the steady state display message SERVICE FAULT/CANNOT CHARGE is generated. No steady state sound sequence is generated. A wrench is further displayed in region R3 of display 56 as an icon.

Now, assume that the battery sensing circuit 48 detects a low battery condition, while the service defibrillator alarm condition remains present. In this instance, a new display message LOW BATTERY is generated and a low battery sound is generated as the new sound sequence. Normally, after the new display message and new sound sequence terminate, the steady state display message LOW BATTERY and delayed continuous alarm steady sound sequence would be produced. In the instant case, however, because the priority of the low battery alarm condition is "5," while the service defibrillator alarm condition priority is "2," the steady state display message and steady state sound sequence for the service defibrillator alarm condition will be produced again. The battery display icon joins the wrench display icon on display 56.

Now, suppose that a silence alarm condition is detected, while the previously detected conditions remain present. This is the highest priority condition. There is, however, no new display message, new sound sequence, steady state display message, or steady state sound sequence associated with this condition. As a result, the previous steady state messages continue to be produced without interruption. Also, a crossed bell display icon is produced and replaces the low battery alarm icon.

As will be appreciated, the routine 60 described above can be altered in a variety of different manners. In that regard, although the eight specific conditions reviewed above relate primarily to instrument operability, a plurality of different patient conditions, treatment conditions, and operator responses can also be incorporated into the message generation scheme. For example, messages relating to patient conditions like heart rate and motion, monitored by sensing circuit 34, may be of interest. Similarly, messages concerning treatment conditions like the amount of energy delivered by the defibrillator circuit 14, or the pacing rate initiated by pacing circuit 16, may be produced in response to outputs from sensing circuits 36 and 38. Further, messages relating to operator responses, as stored by microcomputer 18 in RAM 46, may be of interest.

If desired, messages relating to these different types of instrument readiness, patient, treatment and operator response conditions can be produced by the same region or regions R2 and R3 of display 56. In that case, all of the conditions for which messages are to be produced are prioritized as a single group according to their relative importance.

Alternatively, separate output devices or regions of the same output device may be used to provide messages concerning the instrument readiness, patient, treatment, and operator response conditions. In that case, it may be preferable to use a first prioritization scheme to rank the various instrument readiness conditions, a second scheme to rank the different patient conditions, a third scheme to rank the various treatment conditions, and a fourth scheme to rank the different operator response conditions.

Another variation of potential interest concerns the number of regions R of the display 56 used to produce the different types of messages. More particularly, instead of producing both initial and steady state messages at region R2, separate regions could be used to produce the initial and steady state messages. Alternatively, rather than using one region R2 to produce initial and steady state messages and another region R3 to produce icons, a single region R could be used to produce all three types of messages. In either event, the message prioritization scheme would preferably be altered to rank the different types of messages associated with a single region.

Yet another variation that might be implemented would be to make more extensive use of certain types of messages. In that regard, the voice synthesizer could, for example, be used to produce a verbal prompt corresponding to the initial and steady state display messages.

Those skilled in the art will recognize that the embodiments of the invention disclosed herein are exemplary in nature and that various other changes can be made therein without departing from the scope and the spirit of the invention. Because of the above and numerous other variations and modifications that will occur to those skilled in the art, the following claims should not be limited to the embodiments illustrated and discussed herein.

The embodiments of the invention in which an exclusive property or privilege is claimed are defined as follows:

1. A control system for use with a medical instrument comprising:
    sensing means for monitoring the operation of said instrument to detect a plurality of predetermined conditions;
    message means for generating initial and steady state visible and audible messages indicative of the predetermined conditions; and
    prioritization means for controlling the generation of the initial and steady state messages by said message means in accordance with a predetermined set of parameters including a priority assigned to each of the predetermined conditions detected by said sensing means, wherein the visible messages include an initial display message, steady state display message, and icon.

2. The system of claim 1, wherein the audible messages include an initial sound and a steady state sound.

3. The system of claim 1, wherein said prioritization means causes said message means to generate a flashing initial display message for a predetermined interval of time following the detection of a predetermined condition by said sensing means.

4. The system of claim 3, wherein said prioritization means causes said message means to generate a steady state display message following the initial display message, the steady state message continuing until the predetermined condition is no longer detected by said sensing means or another predetermined condition, having a higher priority associated therewith, is detected.

5. The system of claim 3, wherein said prioritization means causes said message means to generate icons associated with at least the highest priority condition detected by said sensing means.

6. The system of claim 1, wherein said prioritization means causes said message means to generate an initial sound for a predetermined interval of time following the detection of a predetermined condition by said sensing means and a steady state sound following the initial sound, the steady state sound continuing until the predetermined condition is no longer detected by said sensing means or another predetermined condition, having a higher priority associated therewith, is detected.

7. The system of claim 6, wherein said initial sound comprises a first sequence of tones and wherein said steady state sound comprises the repetition of an interval of silence followed by a sequence of tones.

8. A method of controlling the reaction of a medical instrument to a plurality of different conditions identified by the instrument, said method comprising the steps of:
(a) establishing a different priority for each of the different conditions;
(b) associating at least one of a plurality of outputs with each different condition;
(c) producing an output associated with a particular condition identified by the instrument, the particular output produced being dependent upon:
(i) the duration of time since the particular condition was identified;
(ii) whether any other conditions have been identified; and
(iii) the priorities of the particular condition and any other conditions identified.

9. The method of claim 8, wherein said outputs associated with at least some of said different conditions include an initial display message and a steady state display message.

10. The method of claim 9, wherein:
(a) said initial display message is produced immediately after the particular condition is identified and is terminated a predetermined interval of time thereafter; and
(b) said steady state display message is produced after said predetermined interval of time expires and is terminated when one of the following conditions is met:
(i) the particular condition is no longer identified by the instrument;
(ii) a condition, having a higher priority than the particular condition, has been identified by the instrument; and
(iii) a condition, having a lower priority than the particular condition, has been identified by the instrument and a predetermined interval of time has not expired since the other condition was identified.

11. The method of claim 8, wherein said outputs associated with at least some of said different conditions include an initial sound and a steady state sound.

12. The method of claim 11, wherein:
(a) said initial sound is produced immediately after the particular condition is identified and is terminated a predetermined interval of time thereafter;
(b) said steady state sound is produced after said predetermined interval of time expires and is terminated when one of the following conditions is met:
(i) the particular condition is no longer identified by the instrument;
(ii) a condition, having a higher priority than the particular condition, has been identified by the instrument; and
(iii) a condition, having a lower priority than the particular condition, has been identified by the instrument and a predetermined interval of time has not expired since the other condition was identified.

13. The method of claim 8, wherein said outputs associated with at least some of said different conditions include an icon.

14. The method of claim 13, wherein said icon is produced immediately after the particular condition is identified and is terminated when one of the following conditions is met:
(a) the particular condition is no longer identified; and
(b) more than a predetermined number of other conditions, having icons associated therewith and having higher priorities than the particular condition, have been identified by the instrument.

15. The method of claim 8, wherein said different conditions identified by the instrument and the priorities established for each include a silence alarm condition having a first priority, a service defibrillator alarm condition having a second priority, a service alarm condition having a third priority, a very low battery alarm condition having a fourth priority, a low battery alarm condition having a fifth priority, a printer alarm condition having a sixth priority, a tape door open alarm condition having a seventh priority, and a tape fault alarm condition having an eighth condition.

16. A medical system comprising:
a medical instrument;
sensing means for monitoring the operation of said instrument to detect a plurality of predetermined conditions;
initial message generation means for producing an initial message, in response to the sensing of a predetermined condition by said sensing means, for a predetermined interval of time; and
steady state message generation means for producing a steady state message upon the expiration of the predetermined interval of time.

* * * * *

UNITED STATES PATENT AND TRADEMARK OFFICE
CERTIFICATE OF CORRECTION

PATENT NO. : 5,285,792
DATED : February 15, 1994
INVENTOR(S) : S. E. Sjoquist et al.

It is certified that error appears in the above-indentified patent and that said Letters Patent is hereby corrected as shown below:

| COLUMN | LINE | |
|---|---|---|
| On title page, item [56] "Other Information" | 1st Ref. | add --Physio-Control Corporation, LIFEPAK 8: Defibrillator/Monitor with QUIK-PACE Cassette (1986).-- |
| [56] "Other Information" | 2nd Ref. | add --Physio-Control Corporation, LIFEPAK 200: Automatic Advisory Defibrillator (1985).-- |
| 9 | 35 | "as" should read --at-- (third occurrence) |
| 11 | 32 | "present" should read --presence-- |
| 15 | 36 | after "steady" insert --state-- |

Signed and Sealed this

Fifth Day of July, 1994

Attest:

BRUCE LEHMAN

*Attesting Officer*  Commissioner of Patents and Trademarks